United States Patent
Desai

(10) Patent No.: US 8,946,199 B2
(45) Date of Patent: Feb. 3, 2015

(54) CO-ADMINISTRATION OF STEROIDS AND ZOLEDRONIC ACID TO PREVENT AND TREAT SIDE EFFECTS FROM ZOLEDRONIC ACID INFUSION

(76) Inventor: Ketan Desai, Easton, PA (US)

(*) Notice: Subject to any disclaimer, the term of this patent is extended or adjusted under 35 U.S.C. 154(b) by 827 days.

(21) Appl. No.: 12/767,387

(22) Filed: Apr. 26, 2010

(65) Prior Publication Data

US 2011/0263537 A1   Oct. 27, 2011

(51) Int. Cl.
- *A61K 31/56* (2006.01)
- *A61K 31/675* (2006.01)
- *A61K 31/573* (2006.01)

(52) U.S. Cl.
CPC .............. *A61K 31/675* (2013.01); *A61K 31/573* (2013.01)
USPC .......................................... 514/171; 514/182

(58) Field of Classification Search
CPC ............................ A61K 31/675; A61K 31/573
USPC ........................................................ 514/171
See application file for complete search history.

(56) References Cited

PUBLICATIONS

Tauchmanova et al., J. Clin. Endocrinol Metab., 2005;90(2):627-634.*
Durnian et al., Eye, 2005;19:221-222.*
PDR 48th ed., 1994, pp. 1460-1462.*
Poznak, Cancer Control, 2002;9(6):480-489.*
Tanvetyanon et al., Annals of Oncology, 2006;17:897-907.*

* cited by examiner

*Primary Examiner* — San-Ming Hui
(74) *Attorney, Agent, or Firm* — David Bradin

(57) ABSTRACT

Zoledronic Acid is used for treatment of hypercalcemia of malignancy, for the treatment of bone metastasis associated with malignancies such as prostate and breast cancer, for the prevention of and treatment of osteoporosis and for the treatment of Paget's disease. Administration of Zoledronic Acid is complicated by what is described as "post-dosing syndrome" (PDS) and osteonecrosis of the jaw (ONJ). Inflammation may be the cause of these side effects, which could be decreased by the co-administration of steroids. This application is a method of use patent for the co-administration of steroids (oral, IV, IM, rectal, or by inhalation) with Zoledronic Acid and a composition of matter patent for mixing Methyl Prednisolone with Zoledronic Acid for infusion.

13 Claims, No Drawings

CO-ADMINISTRATION OF STEROIDS AND ZOLEDRONIC ACID TO PREVENT AND TREAT SIDE EFFECTS FROM ZOLEDRONIC ACID INFUSION

This application is based on U.S. Provisional Patent US61/135,443 Application filed April, 2010, the entire contents of which are incorporated herein.

FIELD OF THE INVENTION

The present invention relates to the method of use for the co-administration of steroids and Zoledronic Acid to prevent and treat adverse events related to Zoledronic Acid infusion such as post dose symptoms (PDS) and osteonecrosis of the jaw (ONJ). The steroid administration can be oral, parenteral, inhalational, or by suppository. The invention also patents a composition of matter whereby 7.5 mg of Methyl Prednisolone is mixed with 4 or 5 mg of Zoledronic Acid (depending on indication) and infused in Normal Saline.

BACKGROUND OF THE INVENTION

Zoledronic Acid, sold as Zometa/Aclasta/Reclast, is a nitrogen containing bisphosphonate that is used for treatment of hypercalcemia of malignancy, for the treatment of bone metastasis associated with malignancies such as prostate and breast cancer, for the prevention of and treatment of osteoporosis and for the treatment of Paget's disease.

The patent for Zoledronic Acid is held by Novartis and it expires in 2012.

Zoledronic Acid is administered by an intravenous infusion of 4 mg every 3-4 weeks (Zometa) for multiple myeloma and bone metastasis of other malignancies or 5 mg once a year (Aclasta/Reclast) for non-oncology indications. It is also used for the treatment of hypercalcemia of malignancy.

Administration of Zometa is complicated by what is described as "post-dosing syndrome" (PDS) which affects as much as 44% of patients as described in the Zometa Prescribing Information (http://www.pharma.us.novartis.com/product/pi/pdf/Zometa.pdf). The syndrome is characterized by fever, nausea, bone pain, arthralgia, myalgia, chills, etc.

The etiology of this syndrome has not been identified, but is associated with an increase in levels of tumor necrosis factor (TNF), interleukin 6 (IL-6), and gamma interferon ($\gamma$IFN) (Dicuonzo G et al 2003, Schweitzer D H et al 1995, Thiebaud D et al 1997). These cytokines are usually produced by T cells.

Zoledronic acid can cause stimulation of a subset of T cells known as gamma delta ($\gamma\delta$) T cells (Mariani S et al 2005). These cells, specifically V$\gamma$9/V$\delta$2 T cells, can constitute up to 10% of circulating CD3 T cells when stimulated.

Upon stimulation by Zoledronic Acid, these $\gamma\delta$ T cells produce interleukin 2 (IL-2) and TNF. IL-2 in turn can stimulate the production of other cytokines such as IL-6 and $\gamma$IFN. Thus, treatment with Zoledronic Acid can stimulate a subset of T cells that may lead to post-dosing syndrome by production and release of pro-inflammatory cytokines.

Probably the most serious side effect with not only zoledronic acid but all bisphosphonates (BPs) is osteonecrosis of the jaw (ONJ). Patients receiving BPs who have pre-existing dental abnormalities can develop potentially fatal ONJ. Predisposing factors for the development of osteonecrosis of the jaw appear to be dental disease, dental surgery (e.g., tooth extraction), oral trauma, periodontitis, and poor dental hygiene. The risk factors for developing ONJ include trauma, female gender, advanced age, edentulous regions, radiotherapy, chemotherapy, prolonged high dose steroid therapy, blood dyscrasias/metastatic disease, anemia, coagulopathy, surgical dental procedures, alcohol or tobacco use, prior infection, and bisphosphonate therapy (Masoodi, N A 2009).

The incidence of ONJ is less than one in 10,000 in patients with osteoporosis (Masoodi N A, 2009), but is much higher in patients with myeloma and breast cancer (Woo S B, 2006). The severity and lack of predictability make this a serious issue.

While the cause of ONJ is not known, there is some evidence that inflammation plays a role in the pathogenesis (Wilkinson G S et al 2007). This would explain why patients with inflammatory conditions getting prolonged, high dose steroids have a higher incidence of ONJ.

In theory, co-administration of a steroid for a short duration could decrease inflammation and therefore the incidence of ONJ. However, a study to demonstrate this would not be feasible due to the number of patients it would need to demonstrate an effect. A study comparing the incidence of PDS with Zoledronic acid with a Zoledronic Acid and steroid combination is, however, feasible and such a study has been undertaken.

Eight patients with osteoporosis were treated with Zoledronic Acid alone (3 patients) or with the combination of steroids (oral prednisone, 3, and intravenous prednisolone, 2) with Zoledronic Acid. All three patients who got Zoledronic Acid suffered from PDS. In contrast, none of the patients receiving the combination of steroids and Zoledronic Acid suffered from PDS.

This invention asserts that co-administration of Zoledronic Acid with steroids would thus prevent and treat the side effects of Zoledronic Acid infusion more effectively.

SUMMARY OF THE INVENTION

The present invention describes the co-administration of steroids and Zoledronic Acid to prevent or treat the side effects of Zoledronic Acid infusion. The steroids can be oral (provided as a gel, capsule, tablet, powder, liquid, or other pharmaceutically acceptable form), intravenous, intramuscular, inhaled, or a suppository.

DETAILED DESCRIPTION OF THE INVENTION

Zoledronic Acid is to be given as approved by the FDA, i.e. 5 mg for non-oncology indication and 4 mg for oncology indications.

The steroids can be given half an hour before or after the Zoledronic Acid infusion. This is based on the Zoledronic Acid $t_{1/2\alpha}$ 0.24 hours.

The steroids can be given orally (for example, 7.5 mg of Prednisone), by a separate infusion (for example, 7.5 mg of Methyl Prednisolone), mixed in with Zoledronic Acid in the same infusion, intramuscularly, subcutaneously, by rectal suppository, or by inhalation.

The dose of steroids should not exceed the equivalent of 10 mg or prednisone or be less than the equivalent of 5 mg of prednisone.

For a combination of steroid and Zoledronic Acid that can be infused together, 7.5 mg of Methyl Prednisolone can be dissolved with 4 or 5 mg of Zoledronic Acid (4 mg for oncology indications, 5 mg for non-oncology indications) in Normal Saline (up to 100 cc) by swirling gently in room temperature for one minute. It should be used within 5 minutes of mixing if kept at room temperature or within an hour if kept in a refrigerator.

REFERENCES

1. Dicuonzo G, Vincenzi B, Santini D et al. Fever after zoledronic acid administration is due to increase in TNF-alpha and IL-6. J Interferon Cytokine Res 2003; 23: 649-654.
2. Schweitzer D H, Oostendorp-van de Ruit M, Van der Pluijm G et al. Interleukin-6 and the acute phase response during treatment of patients with Paget's disease with the nitrogen-containing bisphosphonate dimethyl-amin hydroxyl-propylidene bisphosphonate. J Bone Miner Res 1995; 10: 956-962.
3. Thiebaud D, Sauty A, Burckhardt P et al. An in vitro and in vivo study of cytokines in the acute-phase response associated with bisphosphonates. Ca Icif Tissue Int 1997; 61: 386-392.
4. Mariani S, Muraro M, Pantaleoni F, Fiore F, Nuschak B, Peola S, et al. Effector T cells and tumor cells as immune targets of zoledronic acid in multiple myeloma. Leukemia 2005; 18: 139-45.
5. Masoodi, Nasseer A. Oral Bisphosphonates and the Risk for Osteonecrosis of the Jaw. BJMP 2009:2(2) 11-15. June 2009).
6. Woo S B, Hellstein J W, Kalmar J R. Systemic Review: Bisphosphonates and osteonecrosis of the jaws. Ann Intern Med 2006;144:753-6.
7. Wilkinson G S, Kuo Y F, Freeman J L, Goodwin J S. Intravenous bisphosphonate therapy and inflammatory conditions or surgery of the jaw: a population based analysis. J Natl Cancer Institute 2007 Jul 4; 99(13): 1016-24.

What is claimed:

1. A method of treating a patient suffering from a disorder ameliorated by treatment with zoledronic acid, while minimizing the side effects associated with the administration of zoledronic acid, comprising administering zoledronic acid and a steroid intravenously, wherein the zoledronic acid and the steroid are administered in a single infusion, wherein the steroid is prednisolone,
   wherein the disorder is selected from the group consisting of hypercalcemia of malignancy, bone metastasis associated with malignancy, osteoporosis, and Paget's disease.
2. The method of claim 1, wherein the dose of prednisolone is around 7.5 mg.
3. The method of claim 1, wherein the disorder is selected from the group consisting of bone metastasis associated with malignancy, osteoporosis, and Paget's disease.
4. The method of claim 3, wherein the disorder is selected from the group consisting of bone metastasis associated with malignancy, and Paget's disease.
5. A method treating a patient suffering from a disorder ameliorated by treatment with zoledronic acid, while minimizing the side effects associated with the administration of zoledronic acid, comprising administering zoledronic acid intravenously, and administering prednisolone about half an hour after the zoledronic acid infusion,
   wherein the disorder is selected from the group consisting of hypercalcemia of malignancy, bone metastasis associated with malignancy, osteoporosis, and Paget's disease.
6. A method treating a patient suffering from a disorder ameliorated by treatment with zoledronic acid, while minimizing the side effects associated with the administration of zoledronic acid, comprising administering zoledronic acid intravenously, and administering prednisolone subcutaneously, intramuscularly, by inhalation, or by a rectal suppository
   wherein the disorder is selected from the group consisting of hypercalcemia of malignancy, bone metastasis associated with malignancy, osteoporosis, and Paget's disease.
7. A method of treating a patient suffering from osteoporosis, comprising administering zoledronic acid and prednisolone intravenously in a single infusion.
8. The method of claim 1, wherein the disorder is hypercalcemia of malignancy.
9. The method of claim 6, wherein the disorder is osteoporosis.
10. The method of claim 6, wherein the disorder is selected from the group consisting of hypercalcemia of malignancy, bone metastasis associated with malignancy, and Paget's disease.
11. The method of claim 6, wherein the disorder is selected from the group consisting of bone metastasis associated with malignancy and Paget's disease.
12. The method of claim 6, wherein the prednisolone is administered subcutaneously, by inhalation, or by a rectal suppository.
13. The method of claim 1, wherein the side effects being minimized are associated with post-dosing syndrome.

* * * * *